United States Patent [19]

D'Muhala et al.

[11] Patent Number: 4,726,907

[45] Date of Patent: Feb. 23, 1988

[54] HYDRAZIDES OF AMINO-POLYACETIC ACIDS AS CHELANTS

[75] Inventors: Thomas D'Muhala; Robert Ward, both of Lebanon, Conn.

[73] Assignee: Nuclear Technology Corp, Amston, Conn.

[21] Appl. No.: 810,131

[22] Filed: Dec. 17, 1985

Related U.S. Application Data

[62] Division of Ser. No. 522,068, Aug. 10, 1983, Pat. No. 4,609,751.

[51] Int. Cl.$^4$ .................................................. C23G 1/14
[52] U.S. Cl. ................................... 252/82; 134/2; 134/22.14; 134/22.19; 134/42; 252/80; 252/148
[58] Field of Search ................ 134/2, 22.14, 22.19, 134/42; 252/80, 82, 148

[56] References Cited

U.S. PATENT DOCUMENTS

| | | | |
|---|---|---|---|
| 3,296,027 | 1/1967 | Jacklin | 252/82 |
| 3,297,580 | 1/1967 | Pitzer | 252/148 |
| 3,308,065 | 3/1967 | Lesinski | 252/82 |
| 3,686,123 | 8/1972 | Hiroshi | 252/82 |
| 3,859,337 | 1/1975 | Herz et al. | 252/82 |

FOREIGN PATENT DOCUMENTS

| | | | |
|---|---|---|---|
| 60-138082 | 7/1985 | Japan | 252/82 |
| 2113254A | 8/1983 | United Kingdom | 252/82 |

*Primary Examiner*—Robert Wax
*Attorney, Agent, or Firm*—Sprung Horn Kramer & Woods

[57] ABSTRACT

Amino-polyacetic acids such as ethylenediaminetetraacetic acid, diethylene triaminepentaacetic acid and nitrilotriacetic acid are reacted with alkanols and then with hydrazine to form the hydrazides which may be converted to carboxyhydrazides, i.e. carbazic acids. The products perform well as chelants and sequestering agents.

2 Claims, No Drawings

HYDRAZIDES OF AMINO-POLYACETIC ACIDS AS CHELANTS

This is a division, of application Ser. No. 522,068, filed Aug. 10, 1983 now U.S. Pat. No. 4,609,757.

The present invention relates to the provision of a novel sequestering agent which performs like, but superior to, ethylenediaminetetraacetic acid with regard to speed, cost, and operating pH.

Where hard water, sea water, corrosion product, or mill scales have been deposited in pipes and on other equipment it is known to remove such deposits by contact with an aqueous solution of sequestering agents of which aminopolyacetic acids have been widely used, e.g. ethylenediaminetetraacetic acid, diethylenetriaminepentaacetic acid, and nitrilotriacetic acid. Similarly, the presence of such sequestering agents in water systems will help prevent the deposit of such scales. These agents perform satisfactorily but require reasonably long contact times and pH's (either acidic or alkaline, depending on the scale to be dissolved) that can be corrosive to the substrate from which the scale is to be removed.

It is accordingly an object of the present invention to provide a novel sequestering agent which performs more quickly and at more acceptable pH's, rendering its use more economical overall.

In accordance with the present invention there is provided a novel sequesteringchelating agent comprising a hydrazide of an amino-polyacetic acid, e.g. nitrilotriacetic acid or an alkylene polyamino-polyacetic acid such as ethylenediaminetetraacetic acid or diethylenetriaminepentaacetic acid. The hydrazide can be a simple hydrazide of hydrazine per se or can be a carboxyhydrazide, i.e. a carbazic acid, produced by reacting the terminal —NH$_2$ groups with alkali metal carbonates.

The invention also extends to the manner of preparing such hydrazides, to compositions containing them and their use.

Hydrazides are advantageously prepared from the aminopolyacetic acids by esterification with a lower alkanol such as methanol or ethanol to form the ester. Advantageously less than the stoichiometric amount is employed, e.g. at most about 0.5 times the stoichiometric amount of acetic acid groups and preferably about 0.3 to 0.45 times, the partial ester thereby being formed. The reaction proceeds in water even at moderate temperatures, e.g. about 100° F.

Substantially simultaneously therewith or subsequent thereto, hydrazine is added, advantageously in from 1.3 to 1.5 times the stoichiometric amount of the acetic acid groups, and the reaction mass is heated for a long time, e.g. 195° F. for 24 hours. Apparently each ester group undergoes hydrazinolysis to form the hydrazide releasing the alcohol which then esterifies another acetic acid group, which goes over to the hydrazide etc., until all the acetic acid groups have been converted.

At the end of the reaction the reaction mass comprises an aqueous solution of the hydrazide containing free hydrazine and alcohol. It can be used as such but it is desirably brought to approximate neutrality, e.g. a pH of about 5.5 to 9.5 and preferably about 8.5 by neutralization with an acid. Acetic acid is suitable but other acids are also useful, except that oxalic acid produces a crystalline precipitate. Citric acid is quite satisfactory.

In accordance with another aspect of the invention, to take full advantage of the excess hydrazine left at the end of reaction, additional amino-polyacetic acid can be added to react therewith, thereby increasing the sequestering capacity. This may itself serve as the pH adjustment or such adjustment can now be effected.

In accordance with yet another aspect of the invention, the hydrazide to be utilized is the carboxyhydrazide, i.e. a hydrogen of the terminal —NH$_2$ group of one or more hydrazide groups is replaced by —COOH. Such products correspond to carbazic acids. Such conversion can be effected by reacting the hydrazide with a carbonate, e.g. an alkali metal carbonate such as potassium carbonate, and heating. Neutralization can now be effected as indicated hereinabove.

The hydrazide solution can be employed directly or with dilution without separation of by-products. The solution finds use where the amino-polyacetic acids themselves were theretofore employed, e.g. reverse osmosis modules and systems, flash and vapor compression evaporators, heating and cooling systems, sea water feed heaters, cooling towers, ultrafiltration systems, heat exchangers, liquor evaporators, and the like, i.e. virtually all systems where scale deposits and/or polyvalent heavy metal deposition might pose a problem.

The present invention also concerns a process for selectively sequestering nickel from a mixture with iron, which process comprises contacting such mixture with a composition comprising water and a hydrazide of an aminopolyacetic acid.

The invention will be further described in the following illustrative example wherein all parts are by weight unless otherwise expressed.

EXAMPLE 1

3.0 Liters of water and 0.25 liter of anhydrous methanol were added to a reaction vessel and heated until the temperature reached 95° F. 6.67 pounds of ethylenediaminetetraacetic acid were then added along with 3.7 liters of 55% solution of hydrazine hydrate. The temperature rose to 120° F. and was brought to 195° F. over 5.5 hours. After 13.5 hours at 195° F. 3.38 pounds of nitrilotriacetic acid were added and, after a day at 195°–200° F. 19.96 pounds of potassium carbonate were added. The vessel was cooled to room temperature and its contents were 3.5 gallons containing 1.4 moles of chelant per liter. Citric acid was added to bring the pH to 8.5.

The chemical reactions involved in the foregoing example can be summarized as follows:

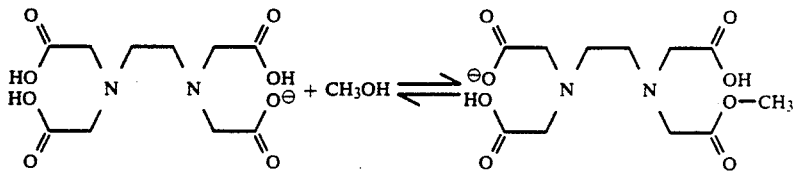

-continued

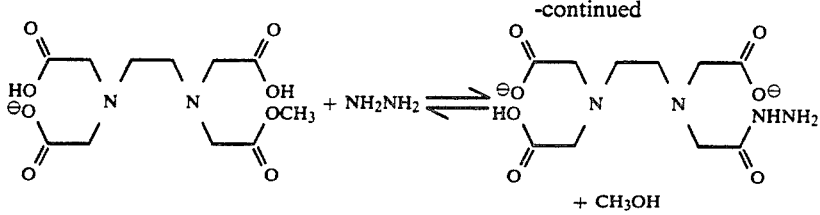

+ CH₃OH

+ H⁺

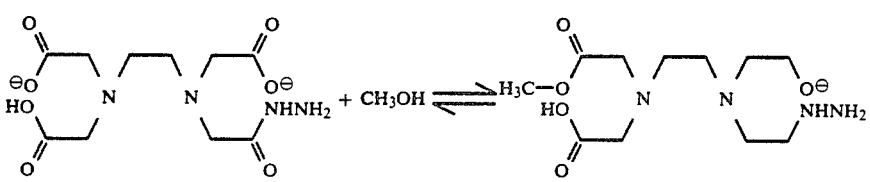

which, upon reaction with potassium carbonate, gives the carbazic acid

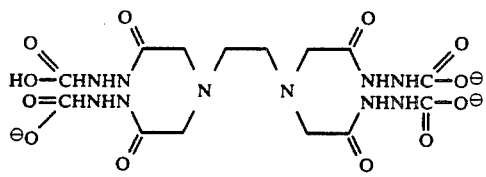

The solution can be used per se or in diluted from. At chelant concentration of about $4 \times 10^{-3}$ or lower, per mole of chelant it will remove iron from scale and hold it in solution to the extent of 5 to 10 moles of iron or more than 20 moles of calcium from a calcium sulfate scale.

The de-scaling activity can be seen in the following examples:

EXAMPLE 2

10 ml of the solution produced in Example 1 and diluted to contain per liter 0.2 mole of chelant and 0.3 mole of citric acid, pH 8.5, were mixed with 90 ml of water from an evaporator containing 36.8915 grams of calcium sulfate scale. The mass was held at 130° F. and the solids were weighed periodically to ascertain any changes. The results obtained were as follows:

| Time in sol'n. | Wght of sample, g | Wght. loss, g |
|---|---|---|
| Start | 36.8915 | — |
| 1 hour | 35.9191 | 0.9723 |
| 2 hours | 34.4425 | 2.3390 |
| 3 hours | 32.8771 | 4.0144 |
| 18 hours | 30.1140 | 6.7775 |

EXAMPLE 3

To a 100 ml solution which consisted of $3.9 \times 10^{-5}$ moles of chelant as produced in example 1 and $4.4 \times 10^{-5}$ moles of citric acid for a final pH of 8.5, 0.0562 g of Fe₃O₄ was added.

The solution was heated to and maintained at a temperature of 130° F. for 16 hours at which time the solution was filtered and the iron content determined.

A spectrophotometric titration at 510 nm with 1,10 phenanthroline revealed that $2.31 \times 10^{-4}$ moles of iron were dissolved in solution.

EXAMPLE 4

A 100 ml cleaning solution consisting of $7.8 \times 10^{-4}$ moles of chelant as produced in Example 1 and $8.6 \times 10^{-4}$ moles of citric acid for a final pH of 8.5 was saturated with Fe₂O₃, FeCr₂O₄2H₂O and Cr₂O₃.

The solution was heated to and maintained at a temperature of 165° F. for 16 hours, after which iron and chromium content was determined.

The metal concentrations were determined via atomic absorption spectrophotometry and found to be:
Iron: $4.66 \times 1 -^{-2}$ Molar
Chromium: $3.33 \times 10^{-3}$ Molar.

What is claimed is:

1. A process for dissolving calcium sulfate scale from an article on which it is deposited which comprises contacting said article with a composition comprising water and a hydrazide of an aminopolyacetic acid in an amount and for a time sufficient to dissolve the calcium sulfate scale.

2. A process for selectively sequestering nickel from a solution or scale containing a mixture of nickel and iron which comprises contacting said solution or scale with a composition comprising water and a hydrazide of an aminopolyacetic acid in an amount and for a time sufficient selectively to sequester or dissolve the nickel.

* * * * *